United States Patent [19]

Biollaz

[11] Patent Number: 4,670,551
[45] Date of Patent: Jun. 2, 1987

[54] EPOXY STEROIDS

[75] Inventor: Michel Biollaz, Riehen, Switzerland

[73] Assignee: Ciba-Geigy Corporation, Ardsley, N.Y.

[21] Appl. No.: 744,444

[22] Filed: Jun. 13, 1985

[30] Foreign Application Priority Data

Jun. 21, 1984 [CH] Switzerland .......................... 3009/84
Sep. 28, 1984 [CH] Switzerland .......................... 4646/84

[51] Int. Cl.⁴ ........................ A61K 31/58; C07J 71/00
[52] U.S. Cl. ..................................................... 540/23
[58] Field of Search .................. 260/239.57; 514/172; 540/23

[56] References Cited

U.S. PATENT DOCUMENTS 4,559,331 12/1985 Nickisch et al. ............... 260/239.57
4,559,332 12/1985 Grob et al. ..................... 260/239.57

FOREIGN PATENT DOCUMENTS 1041534 9/1966 United Kingdom ........... 260/397.45

OTHER PUBLICATIONS

Fieser & Fieser: Steroids; p. 708 (Reinhold Publ. Corporation New York, New York).
Merck Index, 10th Edition, 8610; p. 1254; Merck & Company Rahway, New Jersey, 1983.
Chemical Abstracts, vol. 79, (1973), Abstr. No. 105,471.
Tetrahedron Letters 21: pp. 4163-4166 (1980).
Tetrahedron Letters 23: pp. 167-170 (1982).

*Primary Examiner*—Leonard Schenkman
*Assistant Examiner*—Joseph A. Lipovsky
*Attorney, Agent, or Firm*—Michael W. Glynn; Irving M. Fishman

[57] ABSTRACT

7α-acylthio-9α,11α-epoxy-20-spirox-4-ene-3,21-diones of the formula I

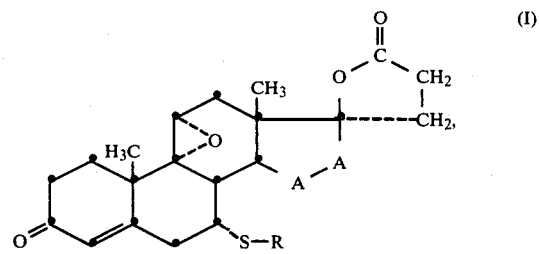

in which R represents lower alkanoyl and —A—A— represents an ethylene or cyclopropylene group, have a high aldosterone-antagonistic activity without significant sexually-specific side-effects and can be used as potassium-protecting diuretics in the treatment of various forms of hyperaldosteronism. The compounds can be obtained by conventional processes of steroid chemistry.

5 Claims, No Drawings

EPOXY STEROIDS

The invention relates to novel steroid compounds having the basic structure of 20-spiroxane, namely lactones of the 7α-acylthio-9α,11α-epoxy-20-spirox-4-ene-3,21-dione type of the formula I

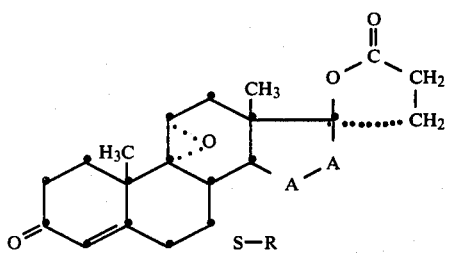

in which R represents lower alkanoyl and —A—A— represents an ethylene or cyclopropylene group. The invention relates also to processes for the manufacture of these compounds, to pharmaceutical compositions containing them and to the manufacture thereof, and to the therapeutic use of these compounds and compositions in warm-blooded animals, especially in human beings.

The compounds according to the invention are distinguished by advantageous biological properties. In particular, they exhibit a strong aldosterone-antagonistic action in that they reduce excessive sodium retention and potassium excretion caused by aldosterone. They therefore have an important role to play as potassium-protecting diuretics in the treatment of diseases that involve electrolyte imbalance, for example in the treatment of cardiac insufficiency, dysrhythmia resulting from potassium deficiency, in Cor pulmonale, cirrhosis of the liver, ascites prophylaxis, diabetes mellitus and hypertonia.

As steroids having an aldosterone-antagonistic action, 20-spiroxane derivatives are especially valuable, see, for example, Fieser and Fieser: Steroids; page 708 (Reinhold Publ. Corp., New York, 1959) and British Patent Specification No. 1 041 534, and of these especially spironolactone (7α-acetylthio-20-spirox-4-ene-3,21-dione) which is generally used in therapy, see the Merck Index, 10th Edition, 8610; page 1254; Merck & Co., Rahway, N.J., U.S.A.; 1983. All the previously used therapeutic agents of this type have, however, a considerable disadvantage in that they always have a certain sexually-specific activity which in the course of treatment, which is usually long-term, sooner or later has an adverse effect. Disorders that can be attributed to the anti-androgenic activity of the known anti-aldosterone preparations are especially undesirable.

As a result of biological testing in a dosage range of approximately from 5 to 50 mg/kg, it has now been found that the introduction of the 9α,11α-epoxy group into the spironolactone molecule results in compounds of the formula I defined above that surprisingly have the full aldosterone-antagonistic action of the basic compound but do not have the undesirable side-effect on the sexual hormone balance. Thus, for example, 7α-acetylthio-9α,11α-epoxy-20-spirox-4-ene-3,21-dione has an aldosterone-antagonistic action of a strength analogous to that of spironolactone (peroral in the Kagawa test with male rats from which the adrenal glands have been removed) but an anti-androgenic action could not be detected in any of the test procedures, even in considerably increased doses.

In the symbol R in the formula I defined above, the lower alkanoyl group is derived from an alkanoic acid, especially a straight-chain alkanoic acid, having from 1 to 4 carbon atoms that is customarily used in steroid chemistry, especially from acetic acid.

The cyclopropylene radical as symbol —A—A— is preferably β-orientated, that is to say forms the 15β,16β-methylene group.

Unless otherwise indicated, the term "lower" used in connection with the definition of a compound or a substituent refers to a compound or a substituent containing no more than 4 carbon atoms.

Preferred compounds of the formula I are, for example, 7α-acetylthio-9α,11α-epoxy-20-spirox-4-ene-3,21-dione and the 15β,16β-methylene analogue thereof.

The compounds of the formula I defined at the beginning can be manufactured according to analogous processes known per se, for example as follows:

(a) in a corresponding 6,7-unsaturated 9α,11α-epoxy compound of the formula II

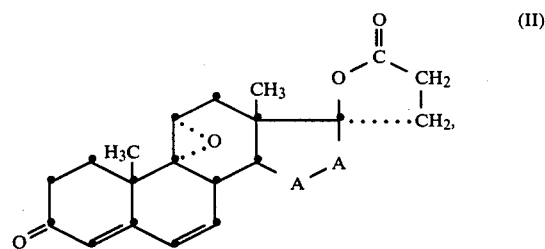

in which —A—A— has the meaning given above, a lower alkanethio acid R-SH (III) in which R has the meaning given above is added to the 6,7-double bond, or (b) in a corresponding 9(11)-unsaturated compound of the formula IV

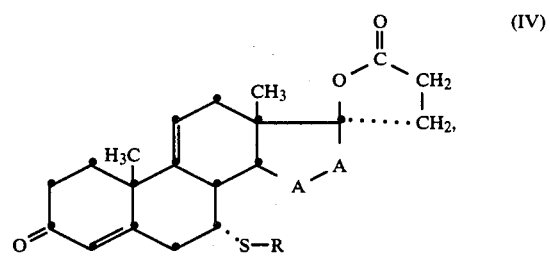

in which R and —A—A— have the meanings given at the beginning, the 9(11)-double bond is expodised.

The addition according to process variant (a) is effected in a manner known per se: for example, preferably the 6,7-dehydro compound (II) in question is heated with a small excess of the thiocarboxylic acid (lower alkanethio acid) of the formula (III), optionally with irradiation with ultraviolet light and/or acid catalysis (for example in the presence of an organic sulphonic acid, such as an aromatic sulphonic acid of the p-toluene- or benzene-sulphonic acid type), in a solvent, especially a lower alkanol, preferably methanol. Although the reaction will take place at room temperature or slightly above room temperature, temperatures of from approximately 50° to approximately 80° C. are preferred; accordingly it is advantageous in the case of relatively low-boiling solvents, for example especially methanol, to carry out the reaction at the boiling temperature; the reaction temperature should not exceed approximately 90°–100° C. The reaction times required can extend to several hours but should be kept to a minimum for optimum results. The reaction is especially carried out under an inert gas, such as nitrogen or argon. In a typical process, the product formed crystallises directly out of the reaction mixture after cooling, optionally after the prior addition of water and/or evaporation of excess solvent; if desired, however, the product may also be isolated or purified in customary manner, for example by chromatography. Addition under these conditions results predominantly in the desired 7α-isomer.

The achievement and, especially, the advantageous result of the process described above is completely surprising, since it was to be expected that the sensitive epoxy ring would be attacked by the acidity of the thiocarboxylic acid to be used as reagent.

The 9α,11α-epoxy-20-spiroxa-4,6-diene-3,21-dione used as starting material is known, see J. Med. Chem. 6, 732–735 (1963), and the analogous starting materials having the methylene group in the 15,16-position can be obtained by analogous processes known per se. The starting materials of the formula III are also known or can be obtained in a known manner.

The compounds of the formula I according to the invention can also be obtained according to process variant (b) by epoxidising the 9(11)-double bond in a corresponding 9(11)-unsaturated compound, that is to say a 7α-acylthio-20-spiroxa-4,9(11)-diene-3,21-dione of the above-defined formula IV.

The epoxidisation of the 9(11)-double bond is effected in a manner known per se by treatment of the starting material of the formula IV with a peroxidic oxidising agent, such as with hydrogen peroxide, preferably in the presence of a nitrile, for example trichloroacetonitrile, or especially with a peroxy acid, preferably an organic peroxy acid, for example an aliphatic peroxy acid, such as, especially, performic acid or peracetic acid, or preferably an aromatic peroxy acid. Of the latter there is advantageously used perbenzoic acid or a substituted perbenzoic acid, such as m-chloroperbenzoic acid, p-nitroperbenzoic acid or monoperoxyphthalic acid (perphthalic acid). The reaction is especially carried out in an inert organic solvent, for example in an alkane, such as pentane, hexane or heptane, a halogenated lower alkane, such as, especially, methylene chloride, chloroform or 1,2-dichloroethane, or an open-chain or cyclic ether, such as, especially, diethyl ether, dioxan or tetrahydrofuran, or an advantageous mixture thereof. The reaction temperature should generally not exceed a temperature at which the spontaneous decomposition of the reactant proceeds more rapidly than does the epoxidisation reaction, and the reaction is especially carried out at room temperature or preferably below room temperature down to approximately −20° C., especially between −10° and +10° C.

Starting materials of the formula IV, if not known, can be manufactured according to analogous processes known per se, for example analogous to the above-described addition of a lower alkanethio acid to 20-spiroxa-4,6,9(11)-triene-3,21-dione, which is itself known, see J. Med. Chem. 6, 732–735 (1963), or, in the case of a 15,16-methylene compound, can be obtained in a manner known per se.

The pharmaceutical preparations of the present invention containing a compound of the formula I can be used especially for the treatment of hyperaldosteronism of widely varied forms. They contain an effective amount of the active ingredient alone or an admixture with inorganic or organic, solid or liquid, pharmaceutically acceptable carriers and, if desired, also in admixture with other pharmacologically or therapeutically valuable substances, and are suitable especially for enteral, for example oral or rectal, or parenteral administration.

Unless specifically indicated, the term "active ingredient" throughout the following text is to be understood as meaning a compound of the formula I as defined at the beginning.

The present invention relates especially to pharmaceutical compositions containing as active ingredient at least one compound of the formula I according to the invention in the form of a sterile and/or isotonic aqueous solution or alternatively in admixture with at least one solid or semi-solid carrier.

The present invention relates also to medicaments, and especially to medicaments in the form of dosage units, that contain at least one of the compounds according to the invention alone or in admixture with one or more carriers, especially those in solid form.

The invention relates especially to medicaments in the form of tablets (including tablets for sucking, granules and pastilles), dragées, capsules, pills, ampoules, dry phials or suppositories containing the above-defined active ingredient alone or in admixture with one or more carriers.

Special forms of these pharmaceutical compositions and medicaments according to the invention are those which, in addition to an aldosterone-antagonistic compound of the formula I according to the invention (which is designated component A in this context), also contain an electrolyte-non-specific diuretic component B.

As such a diuretic component B that is non-specific with regard to electrolyte excretion there come into consideration conventional "classic" diuretics or mixtures thereof that increase diuresis both by a renal and by an extrarenal action on the tissues, especially substances having an inhibitory effect on the reabsorption in the tubules, such as saluretics or ethacrynic acid and analogues thereof. A detailed compilation of suitable diuretics of this type can be found, for example, in U.S. Pat. No. 4 261 985. Especially suitable as the electrolyte-non-specific component B are benzothiadiazine derivatives, such as thiazides and hydrothiazides, also benzenesulphonamides, phenoxyacetic acids, benzofuran-2-carboxylic acids and 2,3-dihydrobenzofuran-2-carboxylic acids. The electrolyte-non-specific component B can comprise a single active ingredient or an advantageous combination of several active ingredients, it also being possible for the active ingredients to belong to several of the mentioned groups of substances. The following conventional diuretics come into special consideration as component B: 1-oxo-3-(3-sulphamyl-4-chlorophenyl)-3-hydroxyisoindoline, 6-chloro-7-sulphamyl-3,4-dihydro-1,2,4-benzothiadiazine 1,1-dioxide, 3-cyclopentylmethyl-6-chloro-7-sulphamyl-3,4-dihydro-1,2,4-benzothiadiazine 1,1-dioxide, 4-(2-methylenebutyryl)-2,3-dichlorophenoxyacetic acid, 4-thenoyl-2,3-dichlorophenoxyacetic acid, (1-oxo-2-methyl-2-phenyl-6,7-dichloro-5-indanyloxy)-acetic acid, 2-chloro-4-furfurylamino-5-carboxybenzenesulphonamide, 2-phenoxy-3-butylamino-5-carboxybenzenesulphonamide and 2-phenoxy-3-[3-(1-pyrrolyl)-propyl]-5-carboxybenzenesulphonamide.

In such pharmaceutical compositions and medicaments according to the invention, the ratio of component A to component B, in relation to the average effective dose in each case, is from approximately 4:1 to approximately 1:4, preferably from approximately 3:2 to approximately 2:3. Since the average effective dose of each specific component is a known value or a value that is simple to determine by known pharmacological test methods, it is readily possible for the person skilled in the art to prescribe within the above-mentioned limits a suitable ratio of the two components for each patient in accordance with the patient's specific complaint, general state of health, individual responsiveness and age, and also the patient's sex.

For example, such combination preparations contain per dosage unit from 15 to 150 mg, especially from 20 to 100 mg, of a compound of the formula I as component A and, as component B, for example, from 10 to 100 mg, especially from 25 to 50 mg, of 2-chloro-5-[3-hydroxy-1-oxoisoindol-3-yl]-benzenesulphonamide or 4-(2-methylenebutyryl)-2,3-dichlorophenoxyacetic acid, from 5 to 50 mg, especially from 12 to 25 mg, of 6-chloro-7-sulphamyl-3,4-dihydro-1,2,4-benzothiadiazine 1,1-dioxide or 2-chloro-4-furfurylamino-5-carboxybenzenesulphonamide, from 2 to 20 mg, especially from 5 to 10 mg, of 2-phenoxy-3-[3-(1-pyrrolyl)-propyl]-5-carboxybenzenesulphonamide, from 0.1 to 1.0 mg, especially from 0.25 to 0.5 mg, of 3-cyclopentylmethyl-6-chloro-7-sulphamyl-3,4-dihydro-1,2,4-benzothiadiazine 1,1-dioxide or 2-phenoxy-3-butylamino-5-carboxybenzenesulphonamide, from 100 to 400 mg, especially 200 mg, of 4-thenoyl-2,3-dichlorophenoxyacetic acid and from 5 to 25 mg, especially 10 mg, of racemic (1-oxo-2-methyl-2-phenyl-6,7-dichloro-5-indanyloxy)-acetic acid, or half the amount of the laevo-form of this acid.

For the treatment of oedema, in a case of moderate severity there are taken daily, for example, from 1 to 3 dosage units that contain amounts by weight of the active ingredients that lie in the region of the upper limit of the above-mentioned especially preferred dosage; a moderately severe case of essential hypertonia is treated, for example, with from 1 to 3 dosage units of which the active ingredient content lies in the region of the lower limit of the especially preferred amounts.

The term "medicament" is used to denote individual separate portions of uniform composition that are suitable for medicinal administration. The phrase "medicament in the form of dosage units" is used in this description to denote individual separate portions of uniform composition that are suitable for medicinal administration and that each contain a specific amount of the active ingredient according to the invention that corresponds to from approximately 0.05 to approximately 2, preferably from approximately 0.1 to approximately 1, daily dose.

The carriers for use in the pharmaceutical compositions (for example granulates) for the manufacture of tablets, dragées, capsules and pills are, for example, the following:

(a) diluents, for example starch, sugars (such as lactose, glucose and saccharose), mannitol, sorbitol and silica, (b) binders, for example carboxymethylcellulose and other cellulose derivatives, alginic acid and salts thereof (such as sodium alginate), gelatine and polyvinylpyrrolidone, (c) humectants, for example glycerine, (d) disintegrators, for example agar-agar, calcium carbonate and sodium bicarbonate, (e) retarding agents for slowing down the absorption of the active ingredient, for example paraffin, (f) absorption accelerators, for example quaternary ammonium compounds, (g) surface-active agents, for example cetyl alcohol and glycerine monostearate, (h) adsorbents, for example kaolin and bentonite, (i) flow-regulators and lubricants, for example talc, calcium stearate, magnesium stearate and solid polyethylene glycols.

These and similar carriers and adjuncts may also serve several of the above-mentioned purposes.

The tablets, dragées, capsules and pills containing the above-mentioned pharmaceutical compositions according to the invention may be provided with the customary coatings and covering materials to which, if desired, colourings or pigments may be added, for example for identification or characterisation purposes. These coatings may be of a composition that renders possible delayed release of the active ingredient; there are suitable for this purpose, for example, waxes and cellulose preparations, such as acetyl cellulose phthalate or hydoxypropylmethylcellulose phthalate.

These compositions may also be processed into microcapsules.

The pharmaceutical compositions according to the invention preferably contain from approximately 0.1 to approximately 99.5% by weight, especially from approximately 1 to approximately 90% by weight, of active ingredient.

The daily dose of the active ingredient of the formula I recommended for a warm-blooded animal weighing 75 kg is approximately from 30 to 300 mg, preferably from 50 to 150 mg, but may greatly exceed or fall below these limits according to species, age and individual responsiveness.

The above-mentioned pharmaceutical compositions, preparations, medicaments and medicaments in the form of dosage units according to the invention are manufactured by means of conventional manufacturing processes known per se in the pharmaceutical industry, for example by means of customary mixing, granulating, tabletting, confectioning, dissolving and lyophilising processes, and, if desired, the operations are carried out under germ-free conditions or an intermediate or finished product is sterilised.

The present invention also relates to the use of the compounds of the formula I for combating widely varied forms of hyperaldosteronism in human beings and other warm-blooded animals, and to a corresponding therapeutic method that is characterised by the administration of an effective dose of at least one of the active ingredients according to the invention alone or together with one or more carriers or in the form of a medicament. The active ingredients according to the invention are administered enterally, for example rectally or especially orally, or parenterally, such as, especially, intravenously. A special form of the therapeutic method according to the present invention is characterised by the administration of a compound of the formula I according to the invention as the aldosterone-antagonistic steroid component A and a diuretic component that is non-specific with regard to electrolyte excretion (component B), either separately at the same time or in admixture, especially in the form of a corresponding pharmaceutical composition or a medicament.

In the following Examples, which further illustrate the invention but do not limit the invention, temperatures are given in degrees Centigrade. Melting points are uncorrected.

EXAMPLE 1

A solution of 6.5 g of 9α,11α-epoxy-20-spiroxa-4,6-diene-3,21-dione in 275 ml of methanol and 11 ml of thioacetic acid is boiled under reflux for 3.5 hours under argon, concentrated to approximately one third by distilling off the solvent at atmospheric pressure and cooled. The reaction product, which crystallises out of the mixture, is filtered with suction and the residue obtained by concentration of the mother liquor is chromatographed over silica gel. Elution with a mixture of hexane/acetone (3:1) yields a further uniform portion of the desired product. The resulting 7α-acetylthio-9α,1-1α-epoxy-20-spirox-4-ene-3,21-dione is crystallised from methylene chloride/methanol; melting point 224° (sintering)—242° (decomposition).

An alternative method of isolating the end product can be carried out as follows: the fully reacted reaction mixture obtained according to the process described above is diluted with 10 ml of water while still hot and concentrated under argon at atmospheric pressure until 190 ml of distillate have been obtained. The product, which crystallises out after cooling, is processed in the manner described above.

In analogous manner, the thioacetic acid can be replaced by thiopropionic acid or thiobutyric acid and the following compounds can be obtained:

(a) 7α-propionylthio-9α,11α-epoxy-20-spirox-4-ene-3,21-dione (amorphous), and (b) 7α-butyrylthio-9α,11α-epoxy-20-spirox-4-ene-3,21-dione (amorphous).

EXAMPLE 2

In a manner analogous to that described in Example 1, 9α,11α-epoxy-15β,16β-methylene-20-spiroxa-4,6-diene-3,21-dione is reacted with thioacetic acid in methanol and processed further according to alternative (b), yielding 7α-acetylthio-9α,11α-epoxy-15β,16β-methylene-20-spirox-4-ene-3,21-dione; melting point 268° (sintering)—292° (decomposition).

The 9α,11α-epoxy-15β,16β-methylene-20-spiroxa-4,6-diene-3,21-dione used as starting material can be manufactured as follows:

(a) A solution of 20 g of 17α,20;20,21-bismethylenedioxypregn-5-ene-3β,11β-diol in 150 ml of pyridine and 150 g of acetic anhydride is heated under reflux for 1 hour. The reaction solution is cooled and, while stirring, poured onto 3000 g of ice flakes and stirred until thawing. The precipitate is filtered with suction and dried in the air; the crude 3β,11β-diacetoxy-17α,20;20,21-bismethylenedioxypregn-5-ene is processed further without purification.

(b) While stirring and cooling externally with ice-water, 20.3 g of the air-dried 3,11-diacetate are added, in portions, to 71 ml of a solution that has been prepared beforehand by introducing, at approximately 0°, 141 g of gaseous hydrogen fluoride into a solution comprising 100 ml of isopropyl alcohol, 48 g of urea and 9.6 ml of water.

While cooling with ice-water, the reaction mixture is stirred for 1 hour, poured carefully into an ice-cold solution of 142 g of sodium sulphite in 1015 ml of water and stirred for 20 minutes. The mixture is extracted with ethyl acetate and washed in succession with saturated sodium chloride solution, ice-cold dilute hydrochloric acid, ice-cold dilute sodium hydroxide solution and again with dilute sodium chloride solution, dried, and concentrated by evaporation under a water-jet vacuum. The residue is chromatographed over 100 times the amount by weight of silica gel. Elution with a mixture of methylene chloride/acetone (95:5) yields uniform fractions which, after being dissolved and recrystallised once from methylene chloride/methanol/ether, yield 3β,11β-diacetoxy-17α,21-dihydroxypregn-5-en-20-one having a melting point of 231°–233°.

(c) 69 g of finely powdered manganese dioxide are added to a solution of 13.8 g of the last-mentioned compound in 207 ml of dioxan and the whole is boiled under reflux for 3 hours. After cooling to room temperature, the solid portion is removed by filtration with suction and washed thoroughly with chloroform. The filtrate is concentrated by evaporation, dissolved in methylene chloride and filtered through 10 times the amount by weight of neutral aluminium oxide. Evaporation of the solvent yields crystalline 3β,11β-diacetoxyandrost-5-en-17-one which, after recrystallisation once from methylene chloride/petroleum ether, melts at 177°–179°.

(d) A mixture of 7.5 g of 3β,11β-diacetoxyandrost-5-en-17-one and 150 mg of p-toluenesulphonic acid in 450 ml of benzene and 7.5 ml of ethylene glycol is boiled under reflux in a water separator for 16 hours. After cooling, the solution is diluted with ethyl acetate and immediately washed with 225 ml of ice-cold saturated sodium chloride solution. After drying, the organic phase is concentrated by evaporation under a water-jet vacuum and the oily 3β,11β-diacetoxy-17,17-ethylenedioxyandrost-5-ene is used for the next step without purification.

(e) At an internal temperature of 5°–10°, a solution of 4.7 g of 3β,11β-diacetoxy-17,17-ethylenedioxyandrost-5-ene in 140 ml of tetrahydrofuran is added dropwise to a stirred suspension of 2.35 g of lithium aluminium hydride in 95 ml of tetrahydrofuran and then rinsed out with 9 ml of tetrahydrofuran, and the mixture is boiled under reflux for 12 hours. The reaction mixture is decomposed at an internal temperature of a maximum of 5° by the careful dropwise addition of a mixture of 9 ml of tetrahydrofuran and 14 ml of ethyl acetate followed by a mixture of 9 ml of tetrahydrofuran and 14 ml of water, and after the addition of 70 g of anhydrous sodium sulphate the mixture is stirred without cooling for a further 30 minutes. Solid portions are removed by filtration with suction over a layer of kieselguhr (subsequent washing with tetrahydrofuran) and the filtrate is concentrated under a water-jet vacuum. The amorphous residue is chromatographed over 50 times the amount by weight of silica gel. Elution with a mixture of methylene chloride/acetone (93:7) and evaporation of the solvent yield uniform 17,17-ethylenedioxyandrost-5-ene-3β,11β-diol which, after being dissolved and recrystallised once from methylene chloride/ether, melts at 123°–125°.

(f) 36.3 g of pyridine hydrobromide perbromide are added to a solution of 16.8 g of 17,17-ethylenedioxyandrost-5-ene-3β,11β-diol in 102 ml of tetrahydrofuran and the whole is stirred at room temperature for 2½ hours. 26.9 g of sodium iodide are added to the mixture, which is then stirred for a further 30 minutes; a solution of 36.3 g of sodium thiosulphate in 50.4 ml of water, and 100 ml of pyridine are added in succession to the mixture and stirring is continued for a further 2 hours at room temperature. The reaction mixture is diluted with 100 ml of water and concentrated under a water-jet vacuum at approximately 45°. The residue is taken up in ethyl acetate and washed in succession with saturated sodium chloride solution, ice-cold dilute hydrochloric acid, ice-cold dilute sodium hydroxide solution and again with saturated sodium chloride solution and dried over sodium sulphate. Distilling off the solvent under a water-jet vacuum results in an amorphous residue comprising crude 16α-bromo-17,17-ethylenedioxyandrost-5-ene-3β,11β-diol. The resulting crude product (13 g) is dissolved in 143 ml of dimethyl sulphoxide, and, while stirring, a mixture of 7 g of potassium tert.-butoxide in 13 ml of dimethyl sulphoxide is added at 45° in the course of 30 minutes and stirring is continued for 20 hours at 50° (bath temperature). The mixture is cooled to room temperature, diluted with approximately 1300 ml of a saturated ammonium chloride solution and taken up in ethyl acetate; the organic phase is washed three times with saturated sodium chloride solution and dried over sodium sulphate. By distilling off the solvent under a water-jet vacuum there is obtained amorphous 17,17-ethylenedioxyandrosta-5,15-diene-3β,11β-diol of a purity adequate for further processing.

(g) 4 ml of a solution of 100 mg of p-toluenesulphonic acid in 10 ml of water are added to a solution of 800 mg of 17,17-ethylenedioxyandrosta-5,15-diene-3β,11β-diol in 40 ml of acetone and the whole is stirred for 6 hours at room temperature. After dilution with 40 ml of water, the acetone is distilled off under a water-jet vacuum and the oily residue is taken up in chloroform and washed with ice-cold saturated sodium bicarbonate solution. Evaporation of the organic solvent yields amorphous 3β,11β-dihydroxyandrosta-5,15-dien-17-one which can be used for the next step without further purification.

(h) Under a nitrogen atmosphere, 1.52 g of 55–60% sodium hydride (as a mineral oil suspension) and 7.57 g of trimethylsulphoxonium iodide are added to dimethyl sulphoxide (64 ml) and the whole is stirred firstly for 30 minutes at room temperature and then for a further 30 minutes at an external temperature of 34°–40°. The mixture is cooled to room temperature and 8 g of 3β,11β-dihydroxyandrosta-5,15-dien-17-one are added and then rinsed out with 26 ml of dimethyl sulphoxide. The reaction mixture is stirred at room temperature for 3 hours, poured onto 1 liter of ice-cold saturated sodium chloride solution, then rinsed out with a small quantity of methyl alcohol and water, acidified with dilute hydrochloric acid and stirred for 30 minutes. The oil that separates out is taken up in ethyl acetate and the organic phase is washed in succession with saturated sodium chloride solution, ice-cold dilute sodium hydroxide solution and again with saturated sodium chloride solution. After drying, the solvent is evaporated off under a water-jet vacuum and the resulting amorphous 3β,11β-dihydroxy-15β,16β-methyleneandrost-5-en-17-one is subjected to the subsequent acetylation without purification.

(i) A solution of 7.9 g of 3β,11β-dihydroxy-15β,16β-methyleneandrost-5-en-17-one in 39.5 ml of pyridine and 39.5 ml of acetic anhydride is left to stand at room temperature for 5 hours, diluted with 800 ml of ice-water and, after standing for 1 hour, extracted with ethyl acetate. The organic phase is washed in succession with saturated sodium chloride solution, ice-cold dilute hydrochloric acid, ice-cold dilute sodium hydroxide solution and again with saturated sodium chloride solution, dried, and concentrated under a water-jet vacuum. Chromatography of the crude product over 30 times the amount by weight of silica gel and elution with a mixture of methylene chloride/acetone (98:2) yield 3β-acetoxy-11β-hydroxy-15β,16β-methyleneandrost-5-en-17-one which, after being dissolved and recrystallised once from methylene chloride/ether/petroleum ether, melts at 209°–211°.

(j) 2.6 ml of a solution of 5% by weight sulphur dioxide in methanesulphonic acid chloride are added to a solution of 1.75 g of 3β-acetoxy-11β-hydroxy-15β,16β-methyleneandrost-5-en-17-one in 10.5 ml of dimethylformamide and 3.5 ml of γ-collidine and the whole is stirred for 20 minutes, the internal temperature being allowed to rise to approximately 45°. While stirring, the mixture, including the precipitate that has formed, is poured onto 17.5 ml of ice-water and stirring is continued for a further 10 minutes. The oil that separates out is taken up in ethyl acetate and washed in succession with saturated sodium chloride solution, ice-cold dilute hydrochloric acid, ice-cold dilute sodium hydroxide solution and again with saturated sodium chloride solution. Evaporation of the solvent yields 3β-acetoxy-15β,16β-methyleneandrosta-5,9(11)-dien-17-one that is uniform according to thin-layer chromatography and is processed further without purification.

(k) While cooling with ice-water, 1.78 g of lithium wire (pieces approximately 5 mm long) are added to a solution of 5.2 g of 3β-acetoxy-15β,16β-methyleneandrosta-5,9(11)-dien-17-one in 127.5 ml of tetrahydrofuran, and then a solution of 12.75 ml of the cyclic ethylene acetal of β-chloropropionaldehyde [2-(3-chloropropyl)-1,3-dioxolan] in 12.75 ml of tetrahydrofuran is added dropwise thereto over a period of 10 minutes and the whole is then stirred for one hour while cooling with ice and for 16 hours at room temperature. 330 ml of ethyl acetate are added to the reaction mixture, which is then stirred for 45 minutes, diluted with further ethyl acetate, washed in succession with saturated sodium chloride solution, ice-cold dilute hydrochloric acid, ice-cold dilute sodium hydroxide solution and again with saturated sodium chloride solution, dried, and concentrated under a water-jet vacuum. The oily crude product is dissolved in a mixture of toluene/ethyl acetate (90:10) and filtered through 10 times the amount by weight of silica gel. After evaporation of the solvent the filtrate yields 4.84 g of amorphous substance. This is dissolved in 363 ml of chloroform; 242 g of acidic aluminium oxide (activity stage 1) are added and the whole is stirred at reflux temperature for 2½ hours, then diluted with a further 363 ml of chloroform and stirred for a further 5 minutes and cooled. The mixture is filtered with suction over kieselguhr, the filter cake is then washed with chloroform and the filtrate is concentrated under a water-jet vacuum. The resulting crude 21-carbaldehyde (4 g) is dissolved in 20 ml of methylene chloride and 80 ml of acetone; 8 ml of an 8N chromium (VI) sulphuric acid solution are added at 5° over a period of 5 minutes and the whole is stirred for 45 minutes while cooling with ice. The mixture is diluted with 80 ml of ice-cold water, stirred for 10 minutes without cooling and extracted with methylene chloride. The organic phase is washed with ice-cold saturated sodium bicarbonate solution and dried. Distilling off the solvent under a water-jet vacuum yields a crystalline crude product which is filtered in a solution in methylene chloride through 5 times the amount by weight of neutral aluminium oxide. By distilling off the solvent from the main fraction there are obtained crystals which, after being dissolved and recrystallised once from methylene chloride/ether, yield 3β-acetoxy-15β,16β-methylene-20-spiroxa-5,9(11)-dien-21-one having a melting point of 241°-243°.

(l) 19 ml of a 1N sodium hydroxide solution are added to a suspension of 1.9 g of 3β-acetoxy-15β,16β-methylene-20-spiroxa-5,9(11)-dien-21-one in 26.6 ml of chloroform and 190 ml of methyl alcohol. The mixture is stirred for 1 hour at room temperature, diluted with 190 ml of water and extracted with one portion of chloroform and one portion of a mixture of chloroform/methanol (90:10). After drying, the combined organic phases are concentrated under a water-jet vacuum and the crystalline crude product is recrystallised once from methylene chloride/ether/petroleum ether. The resulting 3β-hydroxy-15β,16β-methylene-20-spiroxa-5,9(11)-dien-21-one melts at 244°-246°.

(m) 4 ml of solvent are removed by distillation at normal pressure from a suspension of 400 mg of 3β-hydroxy-15β,16β-methylene-20-spiroxa-5,9(11)-dien-21-one in 20 ml of toluene and 3 ml of cyclohexanone. The internal temperature is reduced to approximately 80°, 480 mg of aluminium isopropoxide are added and the whole is stirred under reflux for 2 hours. The solution is cooled to room temperature; a solution of 0.4 ml of acetic acid in 0.8 ml of toluene is added and the whole is evaporated to dryness under a water-jet vacuum four times using 5 ml of water each time. The oily residue is taken up in chloroform, washed in succession with ice-cold dilute hydrochloric acid, water, ice-cold sodium hydroxide solution and again with water, and the organic phase is dried and evaporated under a water-jet vacuum. The amorphous crude product is applied to 50 times the amount by weight of silica gel and chromatographed with a mixture of methylene chloride/acetone (98:2). After being dissolved and recrystallised once from methylene chloride/ether/petroleum ether, the resulting 15β,16β-methylene-20-spiroxa-4,9(11)-diene-3,21-dione melts at 172°-174°.

Variant A (An) A solution of 3.27 g of 15β,16β-methylene-20-spiroxa-4,9(11)-diene-3,21-dione in 16.35 ml of dioxan and 6.54 ml of orthoformic acid trimethyl ester is mixed with 0.654 ml of a solution of 900 mg of p-toluenesulphonic acid in 10 ml of dioxan and 2 ml of ethyl alcohol and the whole is stirred for 4 hours at room temperature, then poured, while stirring, into 430 ml of an ice-cold 0.2N sodium hydroxide solution and stirred intensively for 15 minutes. The precipitate is filtered off with suction, washed with water and dried on the suction-filter. The resulting crude 3-ethoxy-15β,16β-methylene-20-spiroxa-3,5,9(11)-trien-21-one is dissolved in 105 ml of acetone and treated in succession with a solution of 1.13 g of sodium acetate (trihydrate) in 8.84 ml of water and, while cooling to −5°, with 1.55 g of N-bromoacetamide and 1.13 ml of acetic acid. The mixture is stirred for 30 minutes at an internal temperature of approximately −3° and then for a further 15 minutes without cooling; a solution of 0.88 g of potassium iodide in 17.7 ml of water and a solution of 5.58 g of sodium thiosulphate in 17.7 ml of water are added in succession and the mixture is stirred for a further 5 minutes and then diluted with 88 ml of water. The mixture is extracted with chloroform and the organic phase is washed with ice-cold saturated sodium bicarbonate solution. Drying and concentration of the organic phase yield an amorphous residue which is dissolved in 78 ml of dimethylformamide; 3.89 g of lithium carbonate and 3.89 g of lithium bromide are added and the whole is stirred for 3 hours at 100°. The mixture is cooled and, while stirring, poured onto 750 ml of ice-water, and the precipitate is filtered off with suction and washed with water. The filter cake is dissolved in chloroform, dried with sodium sulphate and evaporated to dryness under a water-jet vacuum. The resulting residue is dissolved in methylene chloride, filtered through a column of neutral aluminium oxide (activity II) and eluted with further portions of the same solvent. The eluates are concentrated and the desired 15β,16β-methylene-20-spiroxa-4,6,9(11)-triene-3,21-dione is precipitated in amorphous form by the addition of ether. The product is uniform according to thin-layer chromatography and is suitable for further processing.

(Ao) 75 mg of 90% m-chloroperbenzoic acid are added to a solution of 100 mg of 15β,16β-methylene-20-spiroxa-4,6,9(11)-triene-3,21-dione in 2 ml of methylene chloride and the whole is left to stand for 18 hours at approximately 4° and then for 3 hours at room temperature. After dilution with methylene chloride, the mixture is washed in succession with 10% potassium iodide solution, 10% sodium thiosulphate solution, ice-cold saturated sodium bicarbonate solution and water, dried, and concentrated by evaporation under a water-jet vacuum. The amorphous crude product is chromatographed over a column of silica gel. Elution with a mixture of hexane/ethyl acetate (3:2) yields the desired 9α,11α-epoxy-15β,16β-methylene-20-spiroxa-4,6-diene-3,21-dione, melting point 258° (sintering)–276° (decomposition).

Variant B (Bn) 400 mg of m-chloroperbenzoic acid are added to a solution of 415 mg of 15β,16β-methylene-20-spiroxa-4,9(11)-diene-3,21-dione in 8 ml of methylene chloride and the whole is stirred at room temperature for 80 minutes. The reaction mixture is worked up analogously to process step (Ao) and the crude product is chromatographed over a column of silica gel. Elution with hexane/ethyl acetate (1:1, v/v) yields 9α,11α-epoxy-15β,16β-methylene-20-spirox-4-ene-3,21-dione that is uniform according to chromatography and, after crystallisation from methylene chloride/diisopropyl ether, melts at 264°-266°.

(Bo) 230 mg of 2,3-dichloro-5,6-dicyanobenzoquinone are added to a solution of 310 mg of the last-mentioned compound in 0.2 ml of methylene chloride and 2.1 ml of a 0.2N solution of dry hydrogen chloride gas in dioxan and the whole is stirred at room temperature for 45 minutes. The reaction mixture is filtered through neutral aluminium oxide and the adsorbent is then washed with methylene chloride. Aftr distilling off the solvent there is obtained the desired 9α,11α-epoxy-15β,16β-methylene-20-spiroxa-4,6-diene-3,21-dione which is identical to the product of variant A and, after being dissolved and recrystallised from methylene chloride/diisopropyl ether, melts at 254° (sintering)–275° (decomposition).

EXAMPLE 3

A solution of 414 mg of 7α-acetylthio-20-spiroxa-4,9(11)-diene-3,21-dione and 320 mg of m-chloroperbenzoic acid in 10 ml of dichloromethane is left to stand for 16 hours at 5°. After dilution with a mixture of dichloromethane/ether (1:3), the reaction solution is washed in succession with water, a dilute aqueous potassium iodide solution, a dilute aqueous sodium thiosulphate solution and again with water, dried over sodium sulphate and concentrated in vacuo. The residue is chromatographed over silica gel (60 g). A pre-run containing the unreacted starting material is followed, with hexane/ethyl acetate (2:1), by fractions which, after customary subsequent treatment (see Example 1), yield the desired 7α-acetylthio-9α,11α-epoxy-20-spirox-4-ene-3,21-dione which is identical to the product of Example 1.

EXAMPLE 4

Tablets containing approximately 50 mg of active ingredient, for example 7α-acetylthio-9α,11α-epoxy-20-spirox-4-ene-3,21-dione, are manufactured as follows:

| Composition for 1000 tablets: | |
|---|---|
| active ingredient, very finely ground | 50.0 g |
| powdered sugar (saccharose) | 79.0 g |
| gum arabic | 4.75 g |
| sorbitol | 3.75 g |
| talc | 2.5 g |
| magnesium stearate | 4.9 g |
| mineral oil | 0.1 g |
| carboxymethylcellulose (Na salt) | 5.0 g |
| | 150.0 g |

Manufacture:

The active ingredient is mixed with the powdered sugar and the gum arabic, sieved and granulated by means of an approximately 35% aqueous sorbitol solution. The granulate is forced through a sieve, dried, sieved again and intimately mixed with the remaining adjuncts (talc, magnesium stearate, mineral oil and sodium salt of carboxymethylcellulose). The mixture is compressed in customary manner to form 150 mg tablets.

EXAMPLE 5

Dragées containing approximately 50 mg of active ingredient (for example 7α-acetylthio-9α,11α-epoxy-15β,16β-methylene-20-spirox-4-ene-3,21-dione from Example 2) are manufactured as follows:

| Composition of a dragee core: | |
|---|---|
| active ingredient, micronised | 50.0 mg |
| corn starch | 90.0 mg |
| tricalcium phosphate | 100.0 mg |
| polyvinylpyrrolidone K 25 | 15.0 mg |
| magnesium stearate | 2.0 mg |
| sodium carboxymethylcellulose | 33.0 mg |
| | 290.0 mg |

Manufacture of 50,000 dragée cores

A mixture comprising 2.5 kg of active ingredient, micronised, 4.5 kg of corn starch and 5 kg of tricalcium phosphate is granulated with a solution of 0.75 kg of polyvinylpyrrolidone K 25 in 5 kg of distilled water in a fluidised bed process. To the granulate, which has been dried at 45° and pressed through a sieve of 1 mm mesh width, there are added 0.1 kg of magnesium stearate and 1.65 kg of sodium carboxymethylstarch and the mixture is compressed to form domed tablets of 290 mg.

Manufacture of 6.6 kg of sugar-coated dragées

In a coating vessel of 45 cm diameter, 6 kg of dragée cores are coated in portions with a sugar syrup (2 parts sugar and 1 part by weight distilled water) in which 1.5% polyvinylpyrrolidone K 25 and 1% polyethylene glycol 6000 have been dissolved and 20% talc has been suspended, up to a weight of 360 mg, drying being effected intermediately with warm air at approximately 60°. The sugar syrup (2 parts sugar and 1 part water) is then applied in portions up to a final weight of 400 mg. The dragées are finally given a shiny coating with a solution of 2% of carnauba wax in trichloroethylene.

EXAMPLE 6

Soft gelatine capsules containing 50 mg of active ingredient (see Example 4 or 5) are obtained as follows:

| Composition of a soft gelatine capsule: | |
|---|---|
| active ingredient, micronised | 50.0 mg |
| soya lecithin | 1.5 mg |
| beeswax | 2.5 mg |
| vegetable oil | 110.0 mg |
| vegetable oil, partially hydrogenated | 54.0 mg |
| | 218.0 mg |

Manufacture of 100,000 soft gelatine capsules 5.0 kg of active ingredient, micronised, are suspended in a mixture, prepared by melting, of 0.15 kg of soya lecithin, 0.25 kg of beeswax, 5.4 kg of partially hydrogenated vegetable oil and 11 kg of vegetable oil and, after the punching operation, introduced into gelatine capsules. The gelatine coating consists of approximately 71% gelatine, approximately 28% glycerine (85%) and approximately 1% titanium dioxide and 0.3% p-hydroxybenzoic acid propyl ester. The size of the capsule is 4 minims (oblong shape).

EXAMPLE 7

Film-coated dragées containing 100 mg of active ingredient (see Example 4 or 5) are manufactured as follows:

| Composition of a film-coated dragee core: | |
|---|---|
| active ingredient, micronised | 100.0 mg |
| polyethylene glycol 6000 | 52.0 mg |
| colloidal silica | 5.0 mg |
| stearic acid | 3.0 mg |
| | 160.0 mg |

Manufacture of 10,000 cores 1.0 kg of active ingredient, micronised, is mixed with a melt comprising 0.52 kg of polyethylene glycol (prepared with the addition of 0.05 kg of colloidal silica [specific surface area 200 m$^2$/g]) and, after cooling, pressed through a sieve of 1 mm mesh width. 0.03 kg of pulverulent previously sieved stearic acid is mixed into the granulate and the mixture is compressed to form slightly domed tablets of 160 mg.

Manufacture of 30,000 film-coated dragées

In a coating vessel of 45 cm diameter with warm air being supplied at 35°, 4.8 kg of cores are sprayed continuously with a solution of hydroxypropylmethylcellulose (viscosity 6 cP, 2% solution in water) in distilled water in which 2% talc has been suspended, until each core has been coated with 5 mg of lacquer.

EXAMPLE 8

Tablets containing approximately 50 mg of component A and approximately 25 mg of component B are manufactured as follows:

| Composition of a tablet: | |
|---|---|
| component A, micronised | 50.0 mg |
| component B, micronised | 25.0 mg |
| corn starch | 50.0 mg |
| silica, colloidal | 5.0 mg |
| gelatine | 5.0 mg |
| cellulose, microcrystalline | 75.0 mg |
| sodium carboxymethylstarch | 20.0 mg |
| magnesium stearate | 1.5 mg |
| | 231.5 mg |

Manufacture of 100,000 tablets 5 kg of component A, micronised, 2.5 kg of component B, micronised, and 5.0 kg of corn starch are mixed with 0.5 kg of colloidal silica and the mixture is processed with a solution of 0.5 kg of gelatine in 5.0 kg of distilled water (30° C.) to form a moist mass. This mass is forced through a sieve of 3 mm mesh width and dried at 45° C. (fluidised bed drier). The dry granulate is pressed through a sieve of 0.8 mm mesh width, mixed with a previously sieved mixture of 7.5 kg of microcrystalline cellulose and 2.0 kg of sodium carboxymethylstarch and 0.15 kg of magnesium stearate, and compressed to form tablets weighing 231.5 mg.

As component A there is used, for example, 7α-acetylthio-9α,11α-epoxy-20-spirox-4-ene-3,21-dione and as component B 6-chloro-7-sulphamyl-3,4-dihydro-1,2,4-benzothiadiazine 1,1-dioxide.

In analogous manner it is also possible to use corresponding amounts of the following active ingredients as component B: 2-chloro-5-(3-hydroxy-1-oxoisoindol-3-yl)-benzenesulphonamide or 4-(2-methylenebutyryl)-2,3-dichlorophenoxyacetic acid (each 50 mg), 6-chloro-7-sulphamyl-3,4-dihydro-1,2,4-benzothiadiazine 1,1-dioxide (25 mg), 2-phenoxy-3-butylamino-5-carboxybenzenesulphonamide (0.5 mg), (1-oxo-2-methyl-2-phenyl-6,7-dichloroindanyl-5-oxy)-acetic acid (as a racemate 20 mg, as the laevo-form 10 mg), or 3-cyclopentylmethyl-6-chloro-7-sulphamyl-3,4-dihydro-1,2,4-benzothiadiazine 1,1-dioxide (0.5 mg).

EXAMPLE 9

Soft gelatine capsules containing 50 mg of component A and 12.5 mg of component B are obtained as follows:

| Composition of a soft gelatine capsule: | |
|---|---|
| component A, micronised | 50.0 mg |
| component B, micronised | 12.5 mg |
| soya lecithin | 1.5 mg |
| beeswax | 2.5 mg |
| vegetable oil | 100.0 mg |
| vegetable oil, partially hydrogenated | 54.0 mg |
| | 220.5 mg |

Manufacture of 100,000 soft gelatine capsules 6.25 kg of a uniform mixture of components A and B in a ratio by weight of 4:1, micronised, are processed in the manner described in Example 5 using the same amounts of carriers.

As component A there is used the steroid active ingredient mentioned in Example 8 and as component B 6-chloro-7-sulphamyl-3,4-dihydro-1,2,4-benzothiadiazine 1,1-dioxide.

In analogous manner it is also possible to use corresponding amounts of the following active ingredients as component B: 3-cyclopentylmethyl-6-chloro-7-sulphamyl-3,4-dihydro-1,2,4-benzothiadiazine 1,1-dioxide (0.25 mg), 4-thienyl-2,3-dichlorophenoxyacetic acid (125 mg), 2-chloro-5-(3-hydroxy-1-oxoisoindol-3-yl)-benzenesulphonamide (25 mg) or 2-chloro-4-furfurylamino-5-carboxybenzenesulphonamide (15 mg).

EXAMPLE 10

Film-coated dragées containing 100 mg of component A and 10 mg of component B are manufactured as follows:

| Composition of a film-coated dragee core: | |
|---|---|
| component A, micronised | 100.0 mg |
| component B, micronised | 10.0 mg |
| polyethylene glycol 6000 | 52.0 mg |
| colloidal silica | 5.0 mg |
| stearic acid | 3.0 mg |
| | 170.0 mg |

Manufacture of 10,000 cores 1.1 kg of a uniform mixture of components A and B in a ratio by weight of 10:1, micronised, are mixed with a melt comprising 0.52 kg of polyethylene glycol (prepared with the addition of 0.05 kg of colloidal silica [specific surface area 200 m$^2$/g]) and, after cooling, pressed through a sieve of 1 mm mesh width. 0.03 kg of pulverulent previously sieved stearic acid is mixed into the granulate and the resulting mixture is compressed to form slightly domed tablets of 170 mg.

Manufacture of 30,000 film-coated dragées

In a coating vessel of 45 cm diameter with warm air being supplied at 35° C., 5.1 kg of cores are sprayed continuously with a solution of hydroxypropylmethylcellulose (viscosity 6 cP, 2% solution in water) in distilled water in which 2% talc has been suspended, until each core has been coated with 5 mg of lacquer.

As component A there is used a steroid active ingredient according to Example 8 and as component B 2-phenoxy-3-[3-(1-pyrrolyl)-propyl]-5-carboxybenzenesulphonamide.

In analogous manner it is also possible to use corresponding amounts of the following active ingredients as component B: 6-chloro-7-sulphamyl-3,4-dihydro-1,2,4-benzothiadiazine 1,1-dioxide (25 mg), 2-chloro-5-(3-hydroxy-1-oxoisoindol-3-yl)-benzenesulphonamide (50 mg), 4-(2-methylenebutyryl)-2,3-dichlorophenoxyacetic acid (50 mg), 2-chloro-4-furfurylamino-5-carboxybenzenesulphonamide (20 mg), 2-phenoxy-4-butylamino-5-carboxybenzenesulphonamide (0.5 mg) or 3-cyclopentylmethyl-6-chloro-7-sulphamyl-3,4-dihydro-1,2,4-benzothiadiazine 1,1-dioxide (0.5 mg).

EXAMPLE 11

Dragées containing 40 mg of 7α-acetylthio-9α,11α-epoxy-20-spirox-4-ene-3,21-dione as component A and 10 mg of 6-chloro-7-sulphamyl-3,4-dihydro-1,2,4-benzothiadiazine 1,1-dioxide as component B.

| Composition of a dragee: |
|---|
| Core: |

-continued

| Composition of a dragee: | |
|---|---|
| component A | 40 mg |
| lactose | 160 mg |
| stearyl alcohol | 77 mg |
| polyvinylpyrrolidone | 20 mg |
| magnesium stearate | 3 mg |
| | 300 mg |
| Protective lacquer coating: | |
| 6-chloro-7-sulphamyl-3,4-dihydro-1,2,4-benzothiadiazine 1,1-dioxide | 10 mg |
| sugar, talc, colouring | 190 mg |
| binder q.s. ad | |
| | 500 mg |

Manufacture

The steroid component and the lactose are granulated with the stearyl alcohol melt and a concentrated polyvinylpyrrolidone solution and dried. The resulting mass is sieved and compressed to form compacts weighing 300 mg. These are coated with a layer of protective lacquer and then coated, up to a final weight of approximately 500 mg, with coloured sugar syrup in which the diuretic component B has been dissolved.

EXAMPLE 12

Gelatine capsules containing approximately 50 mg of 7α-acetylthio-9α,11α-epoxy-20-spirox-4-ene-3,21-dione as component A and 125 mg of 4-thenoyl-2,3-dichlorophenoxyacetic acid as component B are manufactured as follows:

| Composition of a dry capsule: | |
|---|---|
| component A | 50.0 mg |
| 4-thenoyl-2,3-dichlorophenoxyacetic acid | 125.0 mg |
| lactose | 124.0 mg |
| magnesium stearate | 1.0 mg |
| | 300.0 mg |

Manufacture of 10,000 dry capsules 0.50 kg of 7α-acetylthio-9α,11α-epoxy-20-spirox-4-ene-3,21-dione, very finely ground, is intimately mixed with 1.25 kg of 4-thenoyl-2,3-dichlorophenoxyacetic acid and pulverised as required; 1.24 kg of very finely ground lactose and 0.01 kg of magnesium stearate are added to the mixture which is then passed through a sieve and homogenised. The powder is sieved and 350 mg portions thereof are introduced dry into gelatine capsules.

What is claimed is:

1. A 9α,11α-epoxy steroid of the formula

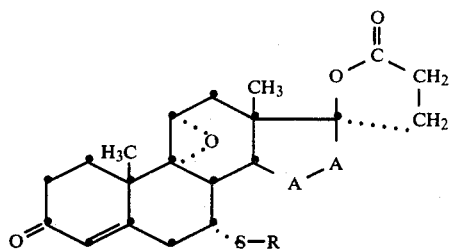

in which R represents lower alkanoyl and —A—A— represents an ethylene or cyclopropylene group.

2. A compound according to claim 1 in which R represents acetyl.
3. A compound according to claim 1 that is 7α-acetylthio-9α,11α-epoxy-20-spirox-4-ene-3,21-dione.
4. A compound according to claim 1 that is 7α-acetylthio-9α,11α-epoxy-15β,16β-methylene-20-spirox-4-ene-3,21-dione.
5. Process for the manufacture of a 9α,11α-epoxy steriod of the formula

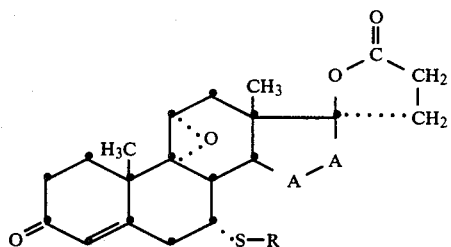

in which R represents lower alkanoyl and —A—A— represents an ethylene or cyclopropylene group, characterised in that (a) in a corresponding 6,7-unsaturated 9α,11α-epoxy compound of the formula

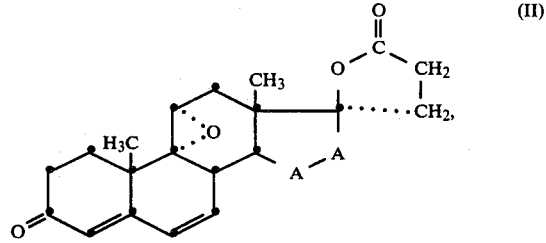

in which —A—A— has the meaning given above, a lower alkanethio acid R-SH (III) in which R has the meaning given above is added to the 6,7-double bond, or (b) in a corresponding 9(11)-unsaturated compound of the formula

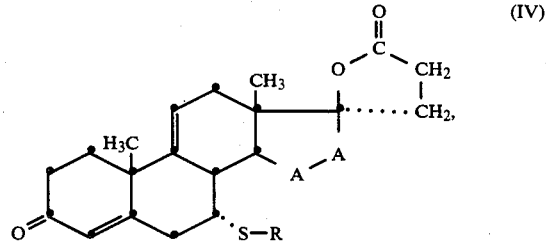

in which R and —A—A— have the meanings given above, the 9(11)-double bond is epoxidised.

* * * * *